United States Patent
Otto

(10) Patent No.: US 11,504,516 B2
(45) Date of Patent: Nov. 22, 2022

(54) PORT CATHETER

(71) Applicant: tricumed Medizintechnik GmbH, Kiel (DE)

(72) Inventor: Karl-Heinz Otto, Kiel (DE)

(73) Assignee: tricumed Medizintechnik GmbH, Kiel (DE)

( * ) Notice: Subject to any disclaimer, the term of this patent is extended or adjusted under 35 U.S.C. 154(b) by 105 days.

(21) Appl. No.: 16/860,651

(22) Filed: Apr. 28, 2020

(65) Prior Publication Data

US 2021/0252266 A1 Aug. 19, 2021

(30) Foreign Application Priority Data

Feb. 18, 2020 (DE) .......................... 102020104235.3

(51) Int. Cl.
*A61M 39/02* (2006.01)
*A61M 5/142* (2006.01)

(52) U.S. Cl.
CPC .... *A61M 39/0247* (2013.01); *A61M 5/14276* (2013.01); *A61M 2039/027* (2013.01); *A61M 2039/0273* (2013.01); *A61M 2039/0282* (2013.01)

(58) Field of Classification Search
CPC .... A61M 2039/027; A61M 2039/0273; A61M 2039/0282; A61M 39/0247; A61M 5/14276

See application file for complete search history.

(56) References Cited

U.S. PATENT DOCUMENTS

2019/0290895 A1* 9/2019 Vogelbaum ........... A61M 39/12

* cited by examiner

*Primary Examiner* — Brandy S Lee
(74) *Attorney, Agent, or Firm* — Diederiks & Whitelaw, PLC.

(57) ABSTRACT

A port catheter includes a port housing and a port chamber formed in the port housing and closed by a septum. The port catheter also includes a first catheter connection communicating with the port chamber for the connection of a first catheter, a second catheter connection for connecting a second catheter connected to an infusion pump and supplying a fluid to the port catheter from the infusion pump, and a third catheter connection communicating with the second catheter connection for connecting a third catheter which discharges the fluid supplied by the infusion pump.

18 Claims, 2 Drawing Sheets

PORT CATHETER

CROSS REFERENCE TO RELATED APPLICATIONS

This application claims priority to German Patent Application No. 10 2020 104 235.3, titled "Port Catheter" and filed on Feb. 18, 2020, which is incorporated herein by reference.

TECHNICAL FIELD

The invention relates to a port catheter having a port housing, a port chamber formed in the port housing and closed by a septum and a first catheter connection communicating with the port chamber for the connection of a catheter.

BACKGROUND

Port catheters of this type are generally known and are used as implants under the skin surface of a patient as permanent access to the abdominal cavity, to the blood vessel system, or to the ventricular system. Percutaneous puncture with a cannula through the septum, which is regularly designed as a silicone membrane, into the port chamber creates a connection to the abdominal cavity, the blood vessel system, or the ventricular system via a catheter connected to the port catheter. In particular, a medicament or a therapeutically effective preparation can be administered to the patient in this way, or body fluid can also be withdrawn taking into account the special circumstances of the port catheter.

A disadvantage of such port catheters is that in cases where sporadic administration of a medication is no longer sufficient, an implantable infusion pump may be implanted in the patient and new or further access to the abdominal cavity, to the blood vessel system or to the ventricular system must be established. This procedure is stressful for the patient and harmful for his organs—also with regard to increasing scarring of tissue.

The object of the invention is therefore to create a versatile port catheter.

SUMMARY OF THE INVENTION

This object is achieved according to the invention by the port catheter described in the preferred embodiments of the invention.

The basic idea of the invention is to create a port catheter via which a first liquid can be infused or aspirated for analysis through the port chamber, and an infusion pump, in particular an implanted infusion pump, can be connected at the same time, which guarantees a constant supply of the patient with a second liquid. According to the invention, two separate liquid lines are created, so that it is also possible to administer different liquids or medications that cannot be stored together. The two liquid-draining catheters are inserted at a common location in the patient's cavity system to be connected to the port catheter, so that the stress on the tissue and the associated stress on the patient is limited to a minimum.

At the same time, it is also possible with the system according to the invention to withdraw body fluid via the port catheter when administering medication through an (implanted) infusion pump and to analyze or even monitor the effect of the medication administration directly at the site of action of the medication.

According to the invention, a port catheter is provided having a port housing, a port chamber formed in the port housing and closed by a septum and a first catheter connection communicating with the port chamber for the connection of a first catheter, in which a second catheter connection for connecting a second catheter connected to an infusion pump and supplying a fluid to the port catheter from the infusion pump is provided, and a third catheter connection communicating with the second catheter connection for connecting a third catheter which discharges the fluid supplied by the infusion pump is provided.

According to a first preferred embodiment, a port catheter is provided with a first side and a second side. The septum is located on the first side of the port catheter. The first catheter connection and the third catheter connection are arranged on the second side of the port catheter opposite the septum. In particular, the septum, the port chamber and the first catheter connection are arranged concentrically to one another, the port chamber particularly preferably having a needle stop.

The second catheter connection is preferably arranged on the side of the port catheter and is therefore easily accessible for connecting the port catheter to an infusion pump.

According to a further preferred embodiment, the port housing has three port housing elements, the first port housing element having a recess for receiving the second port housing element and the third port housing element, the second port housing element having a recess for receiving the third port housing element, and the third port housing element being arranged between the first port housing element and the second port housing element. The second and third port housing elements form the port chamber closed by the septum.

Particularly preferably, a first seal is provided between the first port housing element and the third port housing element and extends around the first catheter connection. The first seal is designed in particular as an O-ring.

Additionally or alternatively, a second seal is provided between the first port housing element and the second port housing element and extends around the third catheter connection. The second seal is also specially designed as an O-ring.

Most preferably, if the first seal and the second seal are designed together, a channel which runs between the second port housing element and the third port housing element and connects the second catheter connection to the third catheter connection is provided and is sealed by the first seal and the second seal.

The port housing elements are preferably made of titanium, stainless steel, ceramic, plastics material, or a composite of the aforementioned materials. The septum is preferably made of silicone and the catheter is preferably made of plastics material, rubber, or silicone.

Regardless of the specific design of the port housing, it is further preferably provided that the first catheter communicating with the port chamber is longer than the second catheter communicating with the infusion pump. In this way, body fluid can be withdrawn via the port chamber without the fluid being adversely affected by an infusion pump connected to the port catheter.

Finally, an implantable system is also claimed which has an implantable infusion pump and a port catheter designed according to the invention, in which the infusion pump is connected to the second catheter connection of the port catheter by the second catheter.

BRIEF DESCRIPTION OF THE DRAWINGS

The invention is explained in greater detail below with reference to a particularly preferably designed exemplary embodiment shown in the attached drawings, which is set up in particular for implantation in the cranium of a Parkinson's patient and for the infusion of liquids into a ventricle. In the drawings.

DETAILED DESCRIPTION OF THE PREFERRED EMBODIMENTS

Figure 1:
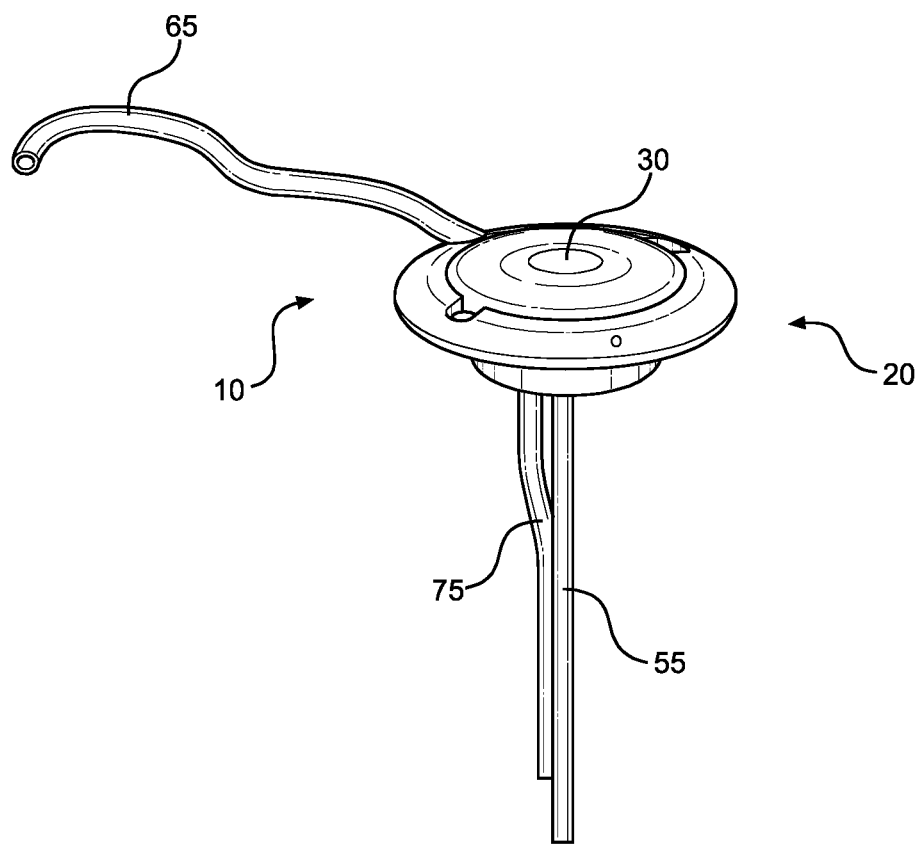
FIG. 1 shows a perspective view of a particularly preferably designed exemplary embodiment according to the invention.

FIG. 1 shows a perspective view of a particularly preferably designed exemplary embodiment according to the invention. In particular, FIG. 1 shows a particularly preferred port catheter 10 having a port housing 20 with a septum 30 embedded in the port housing 20, which closes a port chamber arranged in the port housing. Furthermore, a first catheter 55 communicating with the port chamber, a second catheter 65 connecting the port catheter 10 to an infusion pump (not shown) and a third catheter 75 communicating with the second catheter 65 are illustrated.

Figure 2:
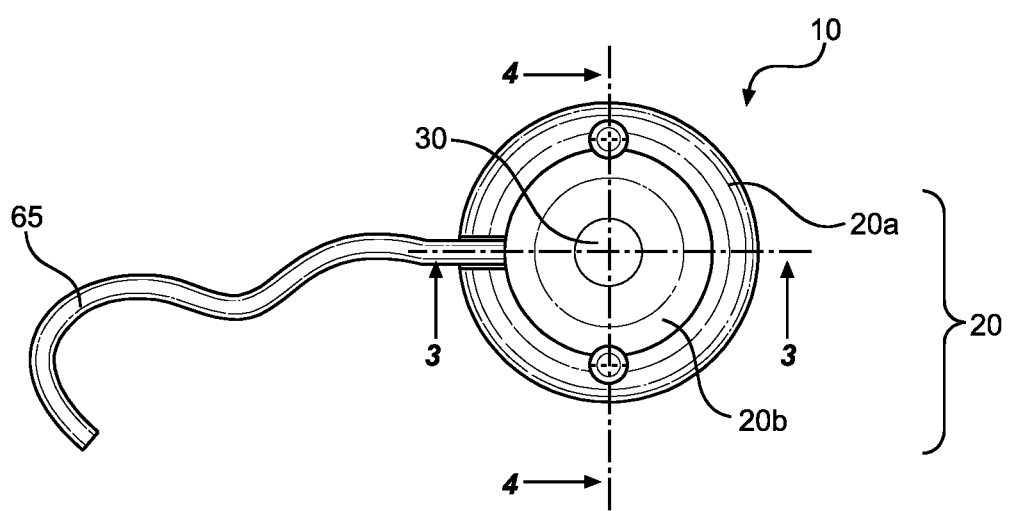
FIG. 2 shows a plan view of the exemplary embodiment shown in FIG. 1.

In the plan view shown in FIG. 2 of the exemplary embodiment shown in FIG. 1, it can be seen that the septum 30 is arranged concentrically in the port housing 20, the port housing 20 being formed from a plurality of port housing elements 20a, 20b arranged concentrically to one another.

Figure 3:
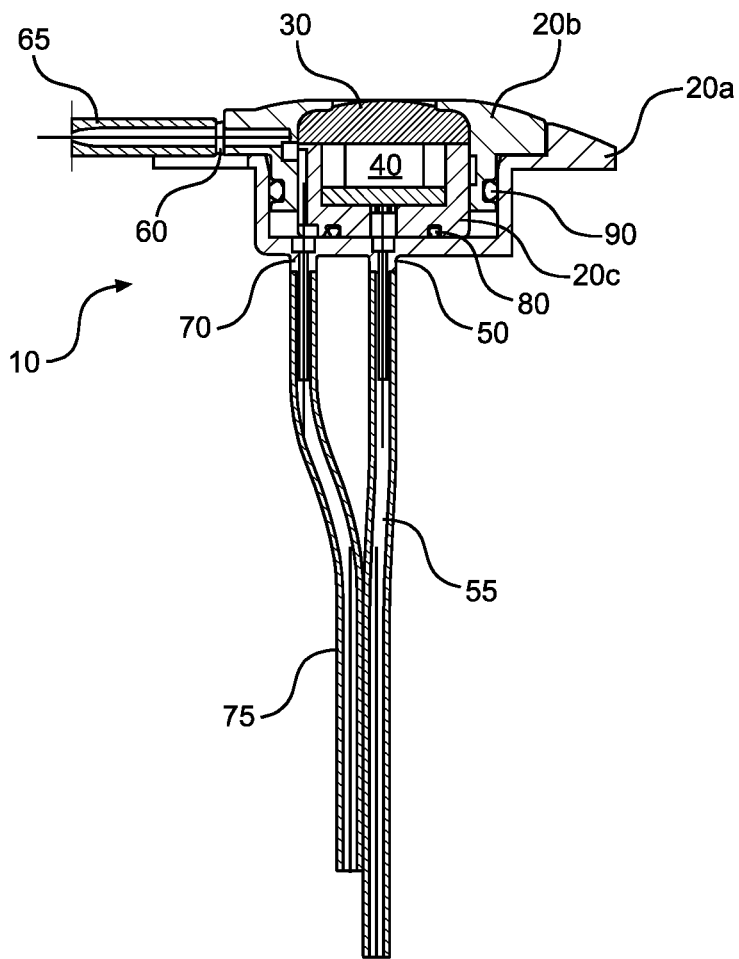
FIG. 3 shows a sectional view of the exemplary embodiment shown above along the line 3-3 illustrated in FIG. 2.

Specifically, FIG. 3 which shows a sectional view of the exemplary embodiment shown above along the line 3-3 illustrated in FIG. 2 illustrates that the port housing 20 has three port housing elements 20a, 20b, 20c, wherein the first port housing element 20a has a recess for receiving the second port housing element 20b and the third port housing element 20c, the second port housing element 20b has a recess for receiving the third port housing element 20c, and the third port housing element 20c is arranged between the first port housing element 20a and the second port housing element 20b. The nested arrangement of these three port housing elements 20a, 20b, 20c enables the port chamber 40 to be easily formed and closed by the septum 30. In this case, the third port housing element 20c can be fixed simply by a fastener securing the second port housing element 20b to the first port housing element 20a.

A first seal 80 arranged between the first port housing element 20a and the third port housing element 20c and extending around the first catheter connection 50 and a second seal 90 arranged between the first port housing element 20a and the second port housing element 20b and extending around the third catheter connection 70 are provided. These seals each ensure a contamination-free fluid line from the infusion pump connected to the second catheter 65 to the third catheter 75 and from the port chamber 40 to the first catheter 55, without the liquids conveyed by the two separate lines coming into contact with one another.

The liquid line between the second catheter connection 60 and the third catheter connection 70 is in particular effected by a channel which runs between the second port housing element 20b and the third port housing element 20c and is sealed by the first seal 80 and the second seal 90. In particular, this channel is designed as an annular channel, so that it is independent of the correct insertion of the second and third port housing elements 20b, 20c into the first port housing element 20a.

The first catheter connection 50 and the third catheter connection 70 are arranged adjacent to one another on the side of the port catheter 10 opposite the septum 30, the second catheter connection 60 being arranged on the side of the port catheter.

Finally, it can be seen that the first catheter 55 is longer than the second catheter 75 and the port chamber 40 has a needle stop.

Figure 4:
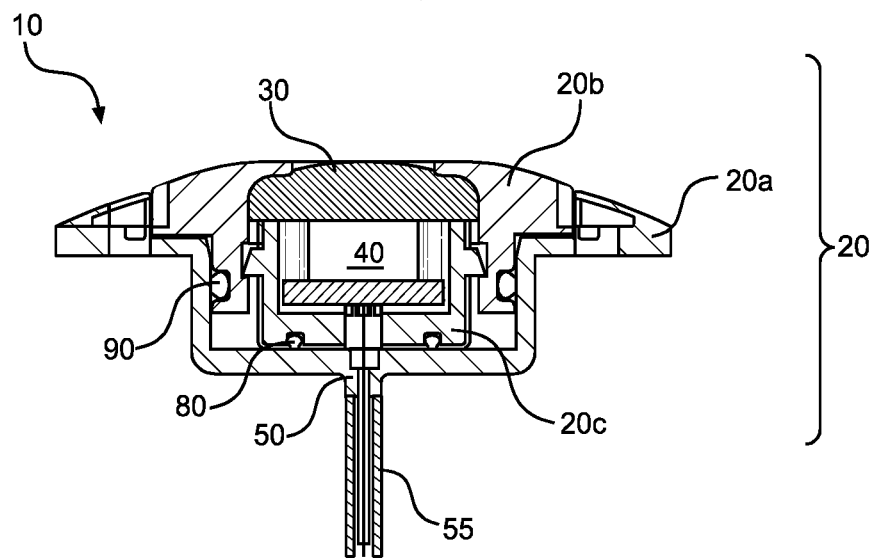
FIG. 4 shows a sectional view of the exemplary embodiment shown above along the line 4-4 illustrated in FIG. 2.

To further illustrate the invention, FIG. 4 shows the exemplary embodiment again in a sectional view along the line 4-4 shown in FIG. 2.

The invention claimed is:

1. A port catheter comprising
a port housing,
a port chamber formed in the port housing and closed by a septum, the port chamber configured to receive a first fluid through the septum,
a first catheter connection communicating with the port chamber for the connection of a first catheter, which discharges the first fluid from the port chamber,
a second catheter connection for connecting a second catheter connected to an infusion pump and supplying a second fluid to the port catheter from the infusion pump, and
a third catheter connection communicating with the second catheter connection for connecting a third catheter which discharges the second fluid supplied by the infusion pump, the port catheter being configured to prevent the first and second fluids from coming in contact with one another.

2. The port catheter according to claim 1, further comprising a first side and a second side and wherein the septum is located on the first side of the port catheter and wherein the first catheter connection and the third catheter connection are arranged on the second side of the port catheter opposite the septum.

3. The port catheter according to claim 1, wherein the second catheter connection is arranged on a side of the port catheter.

4. The port catheter according to claim 1, wherein the port housing has three port housing elements and wherein,
the first port housing element has a recess for receiving the second port housing element and the third port housing element,
the second port housing element has a recess for receiving the third port housing element and
the third port housing element is arranged between the first port housing element and the second port housing element.

5. The port catheter according to claim 4, further comprising a first seal arranged between the first port housing element and the third port housing element and extending around the first catheter connection.

6. The port catheter according to claim 5, further comprising a second seal arranged between the first port housing element and the second port housing element and extending around the third catheter connection.

7. The port catheter according to claim 6, further comprising a channel which runs between the second port housing element and the third port housing element and is sealed by the first seal and the second seal, said channel connecting the second catheter connection to the third catheter connection.

8. The port catheter according to claim 1, wherein the first catheter is longer than the second catheter.

9. The port catheter according to claim 1, wherein the port chamber has a needle stop.

10. An implantable system, comprising
an implantable infusion pump and
a port catheter including
  a port housing,
  a port chamber formed in the port housing and closed by a septum, the port chamber configured to receive a first fluid through the septum,
  a first catheter connection communicating with the port chamber for the connection of a first catheter, which discharges the first fluid from the port chamber,
  a second catheter connection for connecting a second catheter connected to an infusion pump and supplying a second fluid to the port catheter from the infusion pump, and
  a third catheter connection communicating with the second catheter connection for connecting a third catheter which discharges the second fluid supplied by the infusion pump, the port catheter being configured to prevent the first and second fluids from coming in contact with one another, wherein the infusion pump is connected by the second catheter to the second catheter connection of the port catheter.

11. The port catheter according to claim 10, further comprising a first side and a second side and wherein the septum is located on the first side of the port catheter and wherein the first catheter connection and the third catheter connection are arranged on the second side of the port catheter opposite the septum.

12. The port catheter according to claim 10, wherein the second catheter connection is arranged on a side of the port catheter.

13. The port catheter according to claim 10, wherein the port housing has three port housing elements and wherein,
  the first port housing element has a recess for receiving the second port housing element and the third port housing element,
  the second port housing element has a recess for receiving the third port housing element and
  the third port housing element is arranged between the first port housing element and the second port housing element.

14. The port catheter according to claim 13, further comprising a first seal arranged between the first port housing element and the third port housing element and extending around the first catheter connection.

15. The port catheter according to claim 14, further comprising a second seal arranged between the first port housing element and the second port housing element and extending around the third catheter connection.

16. The port catheter according to claim 15, further comprising a channel which runs between the second port housing element and the third port housing element and is sealed by the first seal and the second seal, said channel connecting the second catheter connection to the third catheter connection.

17. The port catheter according to claim 10, wherein the first catheter is longer than the second catheter.

18. The port catheter according to claim 10, wherein the port chamber has a needle stop.

* * * * *